United States Patent [19]

Yoo

[11] 3,937,742

[45] Feb. 10, 1976

[54] HYDROFORMYLATION PROCESS USING CATALYST COMPRISING PLATINUM GROUP METAL ON SUPPORT HAVING SEPARATE ALUMINA PHASE

[75] Inventor: Jin Sun Yoo, South Holland, Ill.

[73] Assignee: Atlantic Richfield Company, Los Angeles, Calif.

[22] Filed: Feb. 7, 1975

[21] Appl. No.: 547,838

Related U.S. Application Data

[63] Continuation-in-part of Ser. No. 17,335, March 6, 1970, abandoned.

[52] U.S. Cl. .......... 260/632 HF; 252/430; 252/460; 260/604 HF; 260/643 G
[51] Int. Cl.² ........................................ C07C 27/22
[58] Field of Search ............... 260/632 HF, 604 HF; 252/460

[56] References Cited
UNITED STATES PATENTS

| | | | |
|---|---|---|---|
| 3,098,030 | 7/1963 | Coonradt et al. | 252/460 |
| 3,235,512 | 2/1966 | Koepernik | 252/460 |
| 3,428,573 | 2/1969 | Reitmeier et al. | 252/460 |
| 3,487,112 | 12/1969 | Paulik et al. | 260/604 HF |
| 3,499,933 | 3/1970 | Pruett et al. | 252/431 P |
| 3,594,425 | 7/1971 | Brader et al. | 260/604 HF |
| 3,733,362 | 5/1973 | Bisle | 260/632 HF |
| 3,855,307 | 12/1974 | Rony et al. | 260/604 HF |

FOREIGN PATENTS OR APPLICATIONS

| | | | |
|---|---|---|---|
| 1,138,601 | 1/1969 | United Kingdom | 260/604 HF |
| 1,411,602 | 8/1965 | France | 260/632 HF |

Primary Examiner—Joseph E. Evans
Attorney, Agent, or Firm—John R. Ewbank

[57] ABSTRACT

A catalyst composition for the hydroformylation, including hydroxyhydroformylation, of $C_2$ to $C_{16}$ olefins to provide alcohols and aldehydes is disclosed. The catalyst contains a hydrido-platinum-group metal-carbonyl, such as hydridopalladium carbonyl, on a solid, acidic, silica-based support material. The catalyst composition can also contain a Group VA electron donor ligand, such as triphenyl phosphine.

5 Claims, No Drawings

HYDROFORMYLATION PROCESS USING CATALYST COMPRISING PLATINUM GROUP METAL ON SUPPORT HAVING SEPARATE ALUMINA PHASE

This application is a continuation-in-part of Ser. No. 17,335, filed Mar. 6, 1970; now abandoned.

This invention relates to a catalyst composition and its use in the hydroformylation, including hydroxyhydroformylation, of olefins. In a particular embodiment, this invention relates to a process for the hydroformylation of pentene and to a catalyst therefor.

Numerous catalysts have been disclosed in the prior art as suitable for the hydroformylation, including hydroxyhydroformylation, of olefins to form low molecular weight alcohols and aldehydes of these olefins. Hydroformylation of olefins with noble metal carbonyl-phosphine complexes (such as platinum, ruthenium, osmium, iridium or rhodium carbonyl-triphenylphosphine complexes) in the liquid phase are shown in U.S. Pat. No. 3,239,571 and in French Pat. No. 1,459,643. The synthesization of propanol by the hydroformylation of ethylene using a palladium chloride catalyst is reported in the Bulletin of the Chemical Society of Japan, Vol. 38 (12), p. 2213 (1965) and Vol. 39 (1), p. 141 (1966). However, in the latter processes, the yield of propanol was low with a hydrogenation reaction being carried out to a larger extent than the hydroformylation.

In U.S. Pat. No. 3,487,112, there is disclosed a solid catalyst system for the hydroformylation of olefins. The catalyst system therein disclosed comprises a solid inert support having dispersed thereon a coordination complex of rhodium, carbon monoxide, a halide and an organo-phosphine, -arsine and/or -stibine ligand.

It has now been found that a solid catalyst of a hydrido-platinum-group metal (e.g., platinum, palladium, rhodium and ruthenium) carbonyl with or without a Group VA electron donor ligand, on a solid acidic, silica-based material exhibits high catalytic activity for the hydroformylation and hydroxyhydroformylation of low molecular weight olefins in the presence or absence of an inert solvent for the production of alcohols and aldehydes under relatively mild conditions. The catalyst composition of the instant invention has highly desirable physical and chemical properties.

In the preparation of the catalyst composition of the present invention, the platinum group metal is provided by salts or complexes of the metal which are soluble in a suitable solvent wherein the impregnation can be performed. Exemplary of such sources are salts such as $MX_n$ where X is a halide, acetate, nitrate, sulfate or phosphate, M represents the platinum group metal and n is the available metal valence; hydrocarbyloxy derivatives, e.g., $M(OR)_n$, where R represents alkyl, aryl, aralkyl, and the like, groups; dihydrocarbyloxy metal carboxylates, i.e., $(RO)_nMOOCR'$, where R and R' are as defined above for R; diphosphine complexes, e.g., $M[(C_6H_5)_2PC_2H_4P(C_6H_5)_2]X_2$, where X is a halide. Also available as metal sources are chelates formed by the platinum-group metals and $\beta$-diketones or $\beta$-ketocarboxylic acid esters and salts of carboxylic acids. Examples of these types of metal sources include $\beta$-diketonato-M, acetylacetonato-M (II), propylacetonato-M (II), benzoylacetonato M, chelates from $\beta$-ketocarboxylic acid esters; salts of saturated and unsaturated monocarboxylic acids, e.g., the platinum-group metal acrylate, acetate, and the like; salts of saturated dicarboxylic acids, e.g., the platinum-group metal adipate, decane-1,10-dicarboxylate, and the like; like salts of corresponding unsaturated dicarboxylic acids, e.g., the platinum-group metal muconate, and the like; salt of cyclic and aromatic carboxylic acids, e.g., the platinum-group metal benzoate, phthalates, and the like; and dialkoxycarboxylates, e.g., M dimethoxyacetate, and the like. In the foregoing, it is preferred that R and R' be lower-alkyl, e.g., of 1 to 6 carbons or, when aryl, contain no more than about ten carbons. Preferred as a platinum-group metal source is the acetylacetonate.

The catalyst composition can contain the platinum-group metal in a small, catalytically effective amount, which can be, for example, from about 0.001 to 1 weight percent metal, measured as the weight of the metal carbonyl, preferably from about 0.005 to 0.02 weight percent. The electron donor ligand, when present in the catalyst of this invention, can often be present in an amount sufficient to yield a molar ratio of ligand to platinum-group metal of about 1:1 to 4:1, preferably about 1.5:1 to 3:1, although either the ligand or metal, preferably the ligand, can be present in excess.

The electron donor liqand component which can also be employed in preparing the catalyst of the present invention is preferably a triorganophosphine corresponding to the general formula $R_3P$ wherein R is essentially a hydrocarbon radical, e.g. alkyl, aryl, alkaryl, aralkyl and cycloalkyl, of from 1 to about 20 carbon atoms, preferably 2 to about 6 carbon atoms, and, more preferably, devoid of olefinic or acetylenic unsaturation; different R groups may, of course, be present in the same phosphine molecule. When the phosphine component contains aromatic groups it is generally preferred that these have mono-cyclic structures, e.g., that the groups be selected from phenyl, alkylphenyl, or phenylalkyl radicals.

Multifunctional phosphines of the formula $R_2$—P—P—$R_2$ such as bis(diphenylphosphine)ethane, may be used in place of the foregoing described unidentate phosphines. Phosphines may also be replaced by other electron donor ligands such as, for example, alkyl, aryl, alkaryl, aralkyl, or cycloalkyl phosphites, arsines, stilbines or bismuthines. Other monodentate or bidentate ligands containing nitrogen donating centers such as pyridine or alpha, alpha-bipyridyl, may also be utilized. It is, however, preferred that triorganophosphines be utilized. Examples of suitable phosphines for the composition of the present invention are triphenylphosphine, trimethylphosphine, tricyclohexylphosphine, tri-n-hexylphosphine, tri-n-decylphosphine, tribenzylphosphine, tri-(4-n-butylphenyl) phosphine, and the like. Generally speaking, the electron donor ligand compounds of Group VA elements of the periodic table, having atomic numbers of 15 to 83 can be used in the catalysts.

The solid support of the catalyst of the present invention is an acidic, silica-based material, e.g., having a D + L activity of at least about 20, preferably at least about 30 when determined according to the method of Birkhimer et al., "A Bench Scale Test Method for Evaluating Cracking Catalysts", Proceedings of the American Petroleum Institute, Division of Refining, Vol. 27 (III), page 90 (1947), and hereinafter referred to as Cat A. The silica-based support preferably has a substantial surface area as determined by the BET nitrogen absorption procedure (JACS, Vol. 60, pp. 309 et seq.)

(1938). The surface area of the support can be at least about 50 square meters per gram, and such surface areas are often up to about 500 or more m²/gm., preferably about 150 to 400 m²/gm. It is preferred that the catalyst support be relatively dry to avoid undue reaction with and loss of catalytic promoting materials. Thus, it is advantageous that the support be calcined, e.g., at temperatures of about 600° to 1500°F. or more, to reduce the water content, but such calcination should not be so severe that the support is no longer catalytically-active.

The support component contains other materials in addition to silica which materials, when combined with silica, provide an acidic material as in, for instance, the case of silica-alumina. Often these materials are one or more oxides of the metals of Groups II, III and IV of the Periodic Table. Examples of the composites contemplated herein under the generic designation of silica-based materials are often composed predominantly of, or even to a major extent of, silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline material such as a crystalline aluminosilicate, for instance, having pore openings in the 6 to 15 Angstrom unit range. The support often contains silica and alumina and such supports, whether naturally-occuring as in acid-treated clays, or a synthetic gel, will frequently contain about 10 to 60, preferably about 15 to 45, weight percent alumina. In addition, such silica-alumina supports can, and preferably do, contain a portion of the alumina as a separate, distinct phase.

A highly preferred catalyst support can be made by combining a silica-alumina hydrogel with a hydrous alumina with or without (preferably without) a crystalline aluminosilicate. An advantageous hydrous alumina component is, when analyzed by X-ray diffraction of dry samples, either one or a mixture of amorphous hydrous alumina and a monohydrate, e.g., boehmite, of less than about 50 A, preferably less than about 40 A, crystallite size as determined by half-width measurements of the (0, 4, 1) X-ray diffraction line calculated by the Debye-Scherrer equation. The mixture of the catalyst precursor components can be dried, e.g., at about 220° to 500°F. to convert the silica-alumina hydrogel to xerogel form. The dried material can then be calcined, e.g., at a temperature of about 700° to 1500°F., preferably about 800° to 1400°F., to provide the active catalyst support. During calcination, the separate hydrous alumina phase of the mixture is converted to a gamma form or other catalytically-active alumina.

In providing the preferred catalyst support precursor for drying, the components can be combined in any suitable manner or order desired, and advantageously each of the components is in the mixture in finely-divided form, preferably the particles are principally less than about 300 mesh in size. The finely-divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about 1/64 to ½ inch or more in diameter and about 1/32 to 1 inch or more in length, before or after drying or calcination.

If formation of the macrosized partcles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline aluminosilicate, preferably the proportions of these ingredients are about 75 to 90%, about 10 to 25% and about 0 to 20%, respectively, If present, the crystalline aluminosilicate is usually at least about 1 weight percent, preferably at least about 5 weight percent, based on the dried support. The alumina content from the silica-alumina xerogel and the separate alumina phase is about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be a silica-alumina hydrogel which contains about 55 to 90, preferably 65 to 75, weight percent silica and about 10 to 45, preferably about 25 to 35, weight percent alumina, on a dry basis. The silica-alumina can be naturally-occurring or can be synthetically prepared by any desired method and several procedures are known in the art. For instance, an amorphous silica-alumina hydrogel can be prepared by coprecipitation or sequential precipitation by either component being the initial material with at least the principal part of the silica or alumina being made in the presence of the other. Generally the alumina is precipitated in the presence of a silica gel. It is preferred that the silica-alumina hydrogel be made by forming a silica hydrogel by precipitation from an alkali metal silicate solution and an acid such as sulfuric acid. Then alum solution may be added to the silica hydrogel slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina. The alumina hydrogel may be prepared, for example, by precipitation of alumina at alkaline pH by mixing alum with sodium aluminate in an aqueous solution or with a base such as soda ash, ammonia, etc. As noted above, the alumina hydrogel can be in the form of amorphous hydrous alumina or alumina monohydrate, e.g., of up to about 50 A crystallite size as determined by X-ray diffraction analysis. The amorphous hydrous alumina generally contains as much combined water as does an alumina monohydrate. Mixtures of the monohydrate and amorphous forms of hydrous alumina are preferred and often, this phase is composed of at least about 25% of each of the separate members.

In preparing the catalyst support, one may separately filter the silica-alumina hydrogel and the hydrous alumina and intimately mix these materials, for instance, by colloidal milling. Although in this particular procedure a low sodium crystalline aluminosilicate can be added after the milling, this ingredient can also be combined before the colloidal milling operation. The mixture is dried, water washed to acceptable concentrations of, for instance, sodium, and redried in the preferred procedure. The drying, especially the initial drying, is advantageously effected by spray drying to give microspheres.

The crystalline aluminosilicate which can be present in catalyst support of the present invention, can have pore openings of 6 to 15 A in diameter, and preferably the pore openings have a diameter of 10 to 14 A. Usually, with a given material, the pores are relatively uniform in size and often the crystalline aluminosilicate particles are primarily less than about 15 microns in size, preferably less than about 10 microns. In the crystalline aluminosilicate the silica-to-alumina mole ratio is often greater than about 2:1 and is usually not above about 12:1, preferably being about 4 to 6:1. The aluminosilicate may be available in the sodium form, and the sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-a and rare earth metals such as cerium, etc. The metals may be present along with the ammonium or hydrogen cations.

The support can also be a naturally-occurring silica-based clay-type mineral, such as kaolin, which contains a major amount of silica and a minor amount of alumina, along with small amounts of other materials, such as sodium oxide, calcium oxide, magnesium oxide, iron oxide, potassium oxide, etc. A typical kaolin clay, after washing and calcining to remove water and other volatile materials which can amount to from about 10 to 20 weight percent of the uncalcined material, can contain from about 50 to 60 weight percent $SiO_2$, about 40 to 50 weight percent $Al_2O_3$, less than about 2 weight percent $Na_2O$ and less than about 1 weight percent of each of CaO, MgO and other metallic oxide impurities. The clay-type support can be fabricated into macrosize form, if desired, of a size of about 1/64 to ½ inch or more in diameter and about 1/32 to 1 inch or more in length.

The catalysts can be prepared by impregnating the silica-based support material with a solution of the platinum-group metal component, e.g., palladium acetylacetonate, ruthenium trichloride, etc., in a solvent, such as ethanol or benzene or the like. The platinum-group metal-containing support can then be contacted with hydrogen and carbon monoxide at a suitable temperature, such as from about 60° to 400°C., preferably from about 150° to 300°C., and at an elevated pressure, e.g., from about 200 to 2500 psig., preferably from about 500 to 2000 psig., to prepare the hydrido-metal-carbonyl complex on the solid support. The hydrogen and carbon monoxide can be introduced separately or as a premixed gas having a molar ratio of hydrogen to carbon monoxide of at least about 0.8:1, e.g., from about 1:1 to 5:1, preferably from about 1.2:1 to 3.5:1. The platinum-group metal-containing support can also be reacted serially with carbon monoxide followed by reaction of the resulting metal-carbonyl supported material with hydrogen under conditions as set forth above for simultaneous reaction.

The platinum-group metal-impregnated support can be reacted with hydrogen and carbon monoxide in the presence of $C_2$ to $C_{16}$ olefins whereby the hydrido-metal-carbonyl supported catalyst is generated in situ concurrently with the hydroformylation of the olefins. Formation of the hydrido-platinum group metal-carbonyl can also be performed in a separate vessel followed by reacting the resulting formation with the support at a temperature of from about 100° to 350°C., and in the presence of hydrogen and carbon monoxide of a molar ratio of hydrogen to carbon of from about 1:1 to 5:1. The reaction of the previously-formed material with the support is also advantageously carried out in the presence of $C_2$ to $C_{16}$ olefins thus generating the solid supported catalyst concurrently with the hydroformylation of olefins.

The electron donor ligand, when present in the catalyst of the present invention, can advantageously be mixed with the platinum-group metal component prior to impregnation of or reaction with the silica-based support material. The two components can be mixed in the presence of a suitable solvent at room temperature or up to about 300°F. The ligand-metal complex usually forms within about 20 to 40 minutes after mixing at elevated temperature. Suitable solvents for the complex-forming reaction include the same solvents which are suitable for use in the final catalyst composition. If desired, however, the complexing may be accomplished in a solvent which is unsuitable for use in the final composition; in this case the resultant complex can first be isolated from the reaction mixture and redissolved, or re-suspended, in a proper solvent which is inert to the final catlyst composition.

Thus, for example, one method of preparing a phosphine-metal complex can involve stirring, preferably at room temperature, a mixture of tri-n-butylphosphine, platinum acetylacetonate and chlorobenzene. In another method, the complex may be prepared by refluxing an alcohol, e.g., ethanol, solution of the phosphine, say tri-n-butylphosphine, and platinum acetylacetonate, preferably at a temperature of about 150° to 250°F., and isolating the resultant complex from the reactant mixture. This approach is often preferred where the metal reagent contains some water of hydration, as the water will be removed from the complex when the latter is separated from the alcohol solvent.

In either case, the platinum-group-electron donor ligand complex can be dissolved in a suitable solvent, e.g., ethanol, methanol, benzene, chlorobenzene, or the like, and charged to a reactor. Hydrogen and carbon monoxide gas can then be introduced separately, or as a premixed gas, in a molar ratio of hydrogen to carbon monoxide of from about 1:1 to 5:1, preferably from about 1.2:1 to 3.5:1, at a temperature of from about 60° to 400°C., preferably from about 150° to 250°C., and a pressure of from about 500 to 3000 psig., preferably from about 700 to 1500 psig., to obtain the hydrido-platinum-group metal carbonyl-electron donor ligand complex. The solid support, in finely-divided form, is combined with the complex in the solvent and the system is agitated for a time sufficient to affix the complex on the support.

The supported catalyst composition of the present invention is effective for hydroformylation or hydroxyhydroformylation of olefinic hydrocarbons, e.g., of 2 to about 16 carbon atoms, preferably 3 to 10 carbon atoms, and is highly desirable for such uses. For example, it is possible to provide alcohols, aldehydes, and the like from aliphatic mono-olefins. The feed can also contain diolefins with conjugated or further apart double bonds. Of particular interest, however, is the selective activity of the present catalyst composition in the hydroformylation of penetene to form hexanol and hexanal. The selectivity of the catalyst of the present invention is exceptional for this type of reaction, while the activity is high as well, resulting in greater efficiency in producing such alcohols and aldehydes. In the prior art, such products are produced in rather minor amounts with the soluble catalyst. With the present solid catalyst, it is possible to obtain such products as the major product.

Hydroformylation can generally be effected by contacting the olefinically-unsaturated feed with hydrogen and carbon monoxide under pressure and in the presence of the catalyst at a temperature of about 100° to 550°C., preferably about 150° to 300°C. Elevated temperatures ordinarily can be maintained by the heat of reaction without external heating means. The reaction is performed at a suitable pressure, e.g. an elevated pressure, which can be up to about 2500 or more psig, preferably about 500 to 2000 psig. The amount of catalyst composition used in the reaction is that sufficient to effect hydroformylation or hydroxyhydroformylation of the feed and often the olefin feed contacts the catalyst at the rate of about 0.1 to about 100, preferably 0.5 to 10, WHSV (weight of olefin per weight of catalyst per hour) in the reaction zone. The hydrogen and carbon monoxide are preferably introduced into the reactor as a premixed gas containing a molar ratio of hydrogen to carbon monoxide from about 1:1 to 5:1, preferably from about 1.2:1 to 3.5:1, although either can be present in excess.

The preparation of an acidic silica-alumina support of this invention is illustrated by Examples I–III, and the support contains a separate phase of alumina.

EXAMPLE I

An alumina hydrogel is prepared as follows:

In a tank containing 5700 gallons of water at 85°F., are dissolved 300 lbs. of soda ash. When the soda ash has been dissolved, 180 gallons of a 39% concentration aqueous sodium aluminate solution are pumped into the tank in about a 15-minute period. The contents of the tank are at about 84°F. Six-hundred gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons of 39% concentration aqueous sodium aluminate solution with, while being added, is also diluted continuously with water at a rate of 35 gallons per minute over a 7½ minute addition period. The contents of the tank are heated to about 100°F., and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet alumina hydrogel is stripped from the drum. This hydrogel analyzes about 50% boehmite having a crystallite size of about 35 A, and 50% amorphous hydrous alumina as determined by X-ray diffraction on dried samples.

EXAMPLE II

A silica-alumina hydrogel is prepared by the following technique:

To a batch tank is added 4,275 gallons of water preheated to 90°F., and 865 gallons of sodium silicate solution (28.8 weight percent $SiO_2$, 40–41.5 Baume at 68°F. and $Na_2O:SiO_2$ ratio of 1:3.2) is added. The batch is stirred for 5 minutes. The concentration of the sodium silicate, as $SiO_2$, in the batch is 6.3 weight percent.

With the batch at 90°F., 302 gallons of 34.5 weight percent sulfuric acid solution at 182°F. are added over a period of 45 minutes. The gel forms about 35 minutes after acid addition is begun. Then the pH is adjusted to 8.0–8.5. The batch is agitated for 10 minutes.

Then 715 gallons of alum (7.8 weight percent, as $Al_2O_3$) is added to the gel over a period of about 36 minutes. The batch is agitated for an additional 5 minutes whereupon 205 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example II and 1740 gallons of the alumina hydrogel filter cake of Example I are mixed together for 1 hour. The finished batch has a pH of 5.5 to 5.6 and a temperature of about 110°F. The aqueous gel mixutre is then pumped to a dewatering filter and the filter cake from said dewatering filter and a portion of aqueous gel are blended to give a gel slurry of about 14 weight percent solids. A portion of this hydrogel mixture was slurried, as a thick flowable paste, with a "Lightnin" stirrer fitted with a cage-beater and a propellor, for about 10 minutes to give a thorough dispersion. The product was stirred 1 minute at 14,500 rpm, in a Waring Blender and dried in a laboratory spray-drier. The spray-dried material was washed with water to acceptable impurity levels and dried at 230°F. The washed and dried material analyzed 0.08% $SO_4$ and less than 25 ppm $Na_2O$. The dried material as such was used as the catalyst support. Extruded forms and tablets (pellets) having diameters of about one-eighth inch and lengths of about one-eighth to one-half inch could also be used. Before use the catalyst support was calcined in a muffle furnace by raising the temperature by 300°F. per hour until 1350°F. was reached. This temperature was then held for 3 hours. The calcined particles had a surface area of about 320 to 340 square meters per gram.

Example IV illustrates the preparation of the catalyst compositions of this invention on the silica-based support.

EXAMPLE IV

A 300cc stainless steel autoclave equipped with a magnetic stirrer was used as a reactor. Palladium acetylacetonate (0.8 m mole) was dissolved in 50 ml benzene in the reactor and 15 g of the microspheroid support of Example III was introduced to the solution. The reactor was tightly closed and purged with hydrogen for 20 minutes, and 30 ml of pentene-1 was fed to the system. The reactor was pressured with a premixed gas ($H_2/CO$ molar ratio of 1:1) to 450 psig and then to 600 psig with hydrogen yielding an $H_2/CO$ molar ratio of 1.6:1. Heating was controlled to raise the temperature of the reactor from 78°F. to 260°C. during about a 1½ hour induction period. The pressure of the reactor assumed 640 psig at this stage. The reactor was then kept at 260°–280°C. for 1½ hours, and the pressure dropped from 640 psig to 540 psig. The reaction was quenched by running cold water through a cooling coil. A clear colorless reaction mixture was removed from the reactor, and the product was analyzed by means of gas chromatographic techniques. About 51% of the pentene-1 feed was reacted to give 24.4% isohexanol, 61.9% n-hexanol and 13.7% unidentified products.

The solid catalyst left inside of the reactor from the first run was rinsed with fresh portions of benzene, and saved for two more runs.

EXAMPLE V

The second run was conducted under conditions similar to those of Example IV. About 58% of the pentene-1 feed was converted to predominantly isohexanol and n-hexanol.

EXAMPLE VI

In the third run, the same reaction was repeated with the 23 hour aged catalyst as described in the preceding runs and under similar conditions. About 54% of the pentene-1 feed was reacted to give 15.5 area % isohexanol, 6.6% n-hexanal, 16.8% isohexanol, 45.1% n-hexanol, and 16.1 unidentified product.

EXAMPLE VII

Ruthenium trichloride (0.3026 g) was dissolved in 90 ml of absolute ethanol to yield a dark-brown solution. 15 grams of microspheres of the catalyst support prepared in Example III were added to the resulting solution, and the system was agitated at room temperature overnight. A light-green supernatant liquid was filtered from dark colored microspheres, and the separated microspheres were rinsed several times with ethanol. The washed microspheres were dried in a vacuum oven (80°C.) for about 15 hours. Dark-brown $RuCl_3$-impregnated microspheres containing about 1.0 weight percent Ru were thus obtained.

A 300 cc autoclave equipped with a magnetic stirrer was employed as a reactor throughout this work. $RuCl_3$-impregnated microspheres (0.6 m mole $Rucl_3$ on 15 g of the catalyst support prepared in Example III) were charged along with 40 ml benzene in the reactor. After the reactor was purged with nitrogen, and then with carbon monoxide, 30 ml of pentene-1, as a typical olefin substrate, was introduced into the system. The reactor was pressured with hydrogen to 560 psig, and then to 860 psig with carbon monoxide, achieving an $H_2/CO$ molar ratio of 1:1. The reactor was then heated by an external heating source. Heating was controlled to attain the temperature and pressure of the reactor at 198°C. and 1345 psig in about 2 hours. At this stage the initial pressure drop was observed. The reactor was ketp at 198°–224°C. for about an hour. The maximum pressure, 1345 psig, dropped to 1030 psig during this period. A yellow reaction mixture was discharged from the reactor and was analyzed by means of gas chromatographic techniques. About 56% of the feed was converted to give 49.1% n-hexanol, 15.7% i-hexanol, 2.2% n-hexanal, 1.1% iso-hexanal, 6.0% unidentified products and 25.9% heavy products. The solid phase left inside of the reactor from the run was saved for an additional run.

EXAMPLE VIII

The same reaction was repeated as described in Example VII using the same catalyst. About 72% of the pentene-1 feed charged to the reactor was converted within a 2¼ hour period. The product yield was 44.0% n-hexanol, 13.9% isohexanol, 1.2% n-hexanal, 0.9% isohexanal, 31.7% heavy products and 8.2% unidentified products.

EXAMPLE IX

Chlorotris(triphenylphosphine)rhodium(I), [$(O_3P)_3RhCl$], was prepared by refluxing an ethanol solution of rhodium(III) chloride in the presence of an excess amount of triphenylphosphine. Chlorotris(triphenylphosphine)rhodium(I) was dissolved in benzene, and the microspheres of Example III were added to the resulting red solution in an autoclave, equipped with a magnetic driven stirrer. Pentene-1 was introduced to the reactor along with benzene. The reaction was performed under conditions similar to Example IV. About 82% of the feed was reacted to give predominantly isohexanol and n-hexanol. The solid catalyst left inside of the reactor from this run was rinsed with fresh portions of benzene, and saved for another run.

The second run was made by injecting pentene-1 in benzene to the rinsed solid catalyst. The reaction conditions were similar to the first run. About 79% of the pentene-1 feed was reacted to 11.1% isohexanal, 20.5% n-hexanal, 7.4% isohexanol, 26.4% n-hexanol and a considerable amount (34.6%) of unidentified products (mostly heavy ends).

EXAMPLE X

Rhodium(III) chloride impregnated microspheres were prepared as follows. Ethanol, (70 ml) was used to dissolve 0.203 g of $RhCl_3.3H_2O$ to give a red solution. The microspheres of Example III (20 g) were added to the solution, and the system was agitated under a nitrogen atmosphere at room temperature for 12 hours. A clear colorless supernatant liquid was left over pink colored microspheres. After the supernant liquid was removed from the microspheres through filtration, the resulting microspheres were rinsed with ethanol several times. The rinsed microspheres were dried under vacuum at 80°C. overnight. Brown microspheres were obtained.

The resulting $RhCl_3$-impregnated microspheres (10 g) were charged with 1.0 m mole triphenyl phosphine ($O_3P$) in 50 ml benzene in a 300 cc autoclave. Soon after the reactor was purged with hydrogen, 30 ml pentene-1 were introduced to the reactor. The reactor was pressured to 500 psig with hydrogen and then to 900 psig with carbon monoxide at 109°F. The reactor was heated to 237°F. in about 30 minutes, and the maximum pressure, 1040 psig, began to drop. The system was maintained at 224°–266°F. for 1½ hours, and the pressure dropped to 750 psig during this period. At this stage, the reaction was quenched by running cold water through a cooling coil in the reactor. A very light-yellow reaction mixture was discharged from the reactor, and the product was analyzed by means of gas chromatographic techniques. The solid catalyst left inside of the reactor was used for six more consecutive runs. The same hydroformylation of pentene-1 was carried out under similar conditions to the preceding run over a 27 hour period. Details of the results obtained from these runs are listed in Tables I and II.

In the fourth to sixth runs propylene was used as a feed while maintaining similar hydroformylation conditions. The results from these runs indicate that the catalytic activity of the solid catalyst persisted at the same level for the hydroformylation of propylene. No effort was made to analyze the product obtained in the 5th run. In the second run as a typical example, about 50% of pentene-1 (19.2 g) was reacted to give 31.1% isohexanal, 24.9% n-hexanal, 0.9% isohexanol, 3.2% n-hexanol, 1.7% unidentified products and 38.1% heavy product. In the sixth run, with the solid catalyst which was aged for 72 hours from the five preceding runs, 10 g. of propylene were reacted in 27% conversion to 39.1% isobutanal, 28.9% n-butanal, 2.0% isobutanol, 1.6% n-butanol, 2.2% 2-ethylhexanal, 20.9% 2-ethyl-2-hexanal, trace amount of 2-ethylhexanol and 5.6% unidentified products.

separate phase of alumina, said alumina resulting from the calcination of a mixture of amorphous hydrous alumina, and alumina monohydrate, the total alumina content of said support being about 20 to 70 weight per cent, said support being prepared by mixing together a separate phase alumina hydrogel with a silica-alumina hydrogel, dewatering the mixture to provide a gel slurry of about 14 weight per cent solids, spray-drying said slurry, washing the spray-dried material, pelletting the washed material, and calcining the pellets at about 1350°F. for about 3 hours to provide calcined particles, said support containing less than 1.5 weight per cent sodium, said reaction being conducted at a temperature of from about 100° to 550°C. at a pressure up to about 2500 psig at an hourly velocity of weight of aliphatic monoolefin hydrocarbon per weight of catalyst of from about 0.5 to about 10, the hydrogen to carbon monoxide mol ratio being from about 1:1 to about 5:1.

2. The process for the hydroformylation of olefin hydrocarbons in accordance with claim 1 wherein the noble metal is palladium, about 0.8 millemole of palla-

TABLE I

| | | Catalyst Composition | | | | Reaction Conditions | | | | |
|---|---|---|---|---|---|---|---|---|---|---|
| Example No. | Run No. | $RhCl_3 \cdot 3H_2O$ mm | $\phi_3P$ mm | Support g | Solv. ml | Catalyst Aged Hrs. | Pressure psig | Temperature °F. | Reaction Time Hrs. | $H_2/CO$ |
| | 1st | 0.4 | 1.0 | 10 | $C_6H_6$ 50 | — | 1040–750 | 224–266 | 1½ | ~1 |
| | 2nd | 0.4 | 1.0 | 10 | 50 | 4 | 935–780 | 217–267 | 2¼ | 1.4 |
| | 3rd | 0.4 | 1.0 | 10 | 40 | 24 | 1095–805 | 217–253 | 3 | ~1 |
| | | | Fresh $\phi_3P$ mm | | | | | | | |
| X | 4th | 0.4 | 0.9 | 10 | 40 | 48 | 1090–980 | 224–255 | 3 | ~1 |
| | 5th | 0.4 | 0.9 | 10 | 40 | 53 | 1360–1300 | 264–302 | 2 | ~1 |
| | 6th | 0.4 | 0.9 | 10 | 40 | 72 | 1340–790 | 222–300 | 4 | 1 |
| | | | | | $CH_3OH$ | | | | | |
| | 7th | 0.4 | 0.9 | 10 | 50 | 82 | 1600–1340 | 240–302 | 5½ | 1 |

TABLE II

| | | | | | Product Distribution | | | | | |
|---|---|---|---|---|---|---|---|---|---|---|
| Example No. | Run No. | Feed | g | Conv. % | $iC_6$-Al | $nC_6$-Al | $iC_6$-OH | $nC_6$-OH | Unknown | Heavy End |
| | 1st | $C_5$=1 | 19.2 | 44 | 31.9 | 31.8 | 0.7 | 3.6 | 3.1 | 28.9 |
| | 2nd | " | 19.2 | 50 | 31.1 | 24.9 | 0.9 | 3.2 | 1.7 | 38.1 |
| X | 3rd | " | 12.8 | 31 | 30.6 | 37.9 | 0.3 | 0.6 | 1.1 | 29.8 |
| | 4th | $C_3$= | 18.0 | 25 | — | — | — | — | 6.6 | 5.1 |
| | 6th | $C_3$= | 10.0 | 27 | — | — | — | — | 5.6 | — |

The invention claimed is:

1. In a process for the hydroformylation reaction of an aliphatic monoolefin hydrocarbon of 2 to about 16 carbon atoms in the liquid phase, the improvement which comprises conducting said hydroformylation reaction in contact with a catalyst composition which comprises a minor, catalytically effective amount of a noble metal selected from; the group consisting of rhodium, ruthenium, platinum, and palladium on a major amount of a solid, acidic, silica-based support of silica-alumina containing a separate phase of alumina, the total catalyst composition containing 0.001 to 1 weight per cent of said noble metal, said support being calcined and comprising 45 to 95 weight per cent amorphous acidic silica-alumina having a Cat-A activity of at least 20 and about 5 to 55 weight per cent of said dium being carried by about 15 g. of carrier, the temperature is about 260°–280°C. and the pressure is about 640 psig, and the hydrocarbon is pentene-1.

3. The process of claim 1 wherein said hydrocarbon is pentene-1, and normal hexanol is the principal product.

4. The process of claim 1 wherein the hydroformylation is conducted at a temperature of from about 100° to 350°C. and a pressure within the range from 500 to 2000 psig and the noble metal is rhodium, about 0.4 millemole of rhodium being deposited on about 10 g. of said support.

5. The process of claim 4 wherein said hydrocarbon is pentene-1 and normal hexanol is the principal product.

\* \* \* \* \*